US00PP30271P3

(12) United States Plant Patent
Biancheri

(10) Patent No.: US PP30,271 P3
(45) Date of Patent: Mar. 5, 2019

(54) ***RANUNCULUS ASIATICUS* PLANT NAMED 'ABALCHERA'**

(50) Latin Name: *Ranunculus asiaticus*
Varietal Denomination: ABALCHERA

(71) Applicant: Alberto Biancheri, Camporosso Mare (IT)

(72) Inventor: Alberto Biancheri, Camporosso Mare (IT)

(73) Assignee: Impresa Individuale Biancheri Alberto (IT)

( * ) Notice: Subject to any disclaimer, the term of this patent is extended or adjusted under 35 U.S.C. 154(b) by 0 days.

(21) Appl. No.: 15/731,525

(22) Filed: Jun. 20, 2017

(65) Prior Publication Data

US 2018/0020590 P1 Jan. 18, 2018

(30) Foreign Application Priority Data

Jul. 13, 2016 (QZ) ..... PBR 2016/1775

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
See application file for complete search history.

*Primary Examiner* — Anne Marie Grunberg
(74) *Attorney, Agent, or Firm* — Cassandra Bright

(57) ABSTRACT

A new and distinct *Ranunculus* cultivar plant named 'ABALCHERA' is disclosed, characterized by the production of large flowers that are uniquely colored creamy peach. Flower stems are exceptionally long. The new variety is a *Ranunculus*, normally produced as a cut flower and also potentially useful as an ornamental plant.

2 Drawing Sheets

Figure 1:
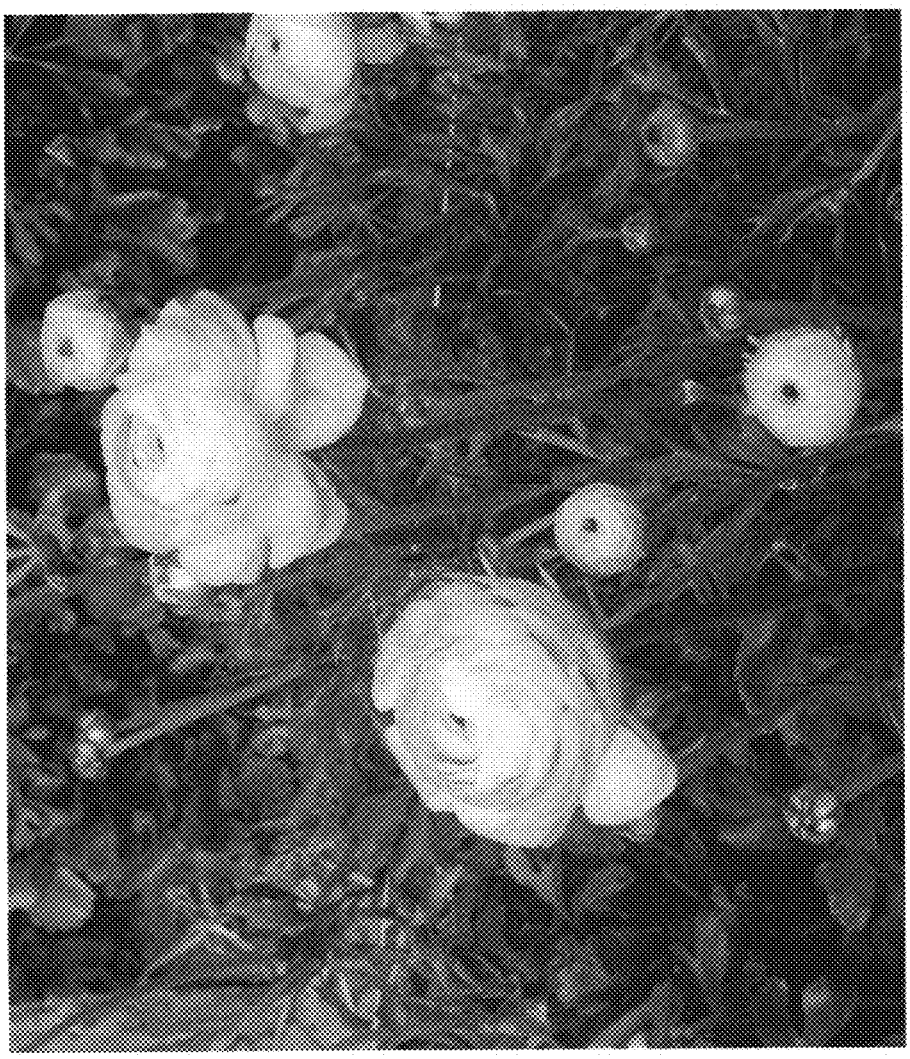
Figure 3:
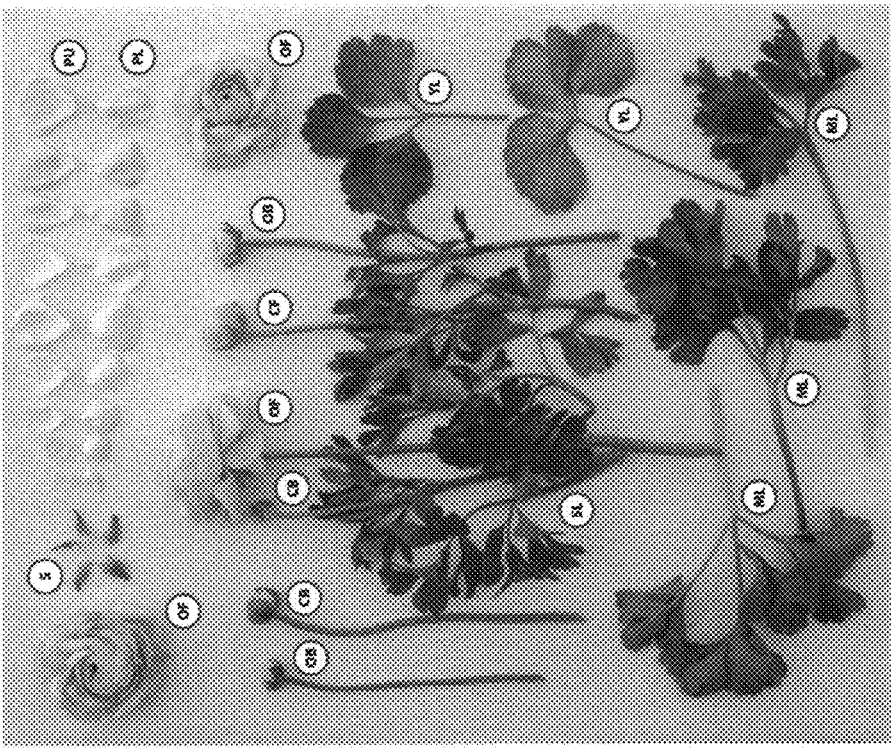

Latin name of the genus and species: *Ranunculus asiaticus*.

Variety denomination: 'ABALCHERA'.

BACKGROUND OF THE INVENTION

The new *Ranunculus* cultivar is a product of a planned breeding program conducted by the inventor, Alberto Biancheri in Camporosso Mare, Italy. The cross resulting in this new variety was made during 2008.

The seed parent is the, unpatented, proprietary variety referred to as *Ranunculus* 'A5-01'. The pollen parent is the unpatented, proprietary variety referred to as *Ranunculus* '68CMT03'. The new variety was discovered in 2013 by the inventor in a group of seedlings resulting from the 2008 crossing, in a research greenhouse in Camporosso Mare, Italy.

Asexual reproduction of the new cultivar was first performed by vegetative division of buds sprouting from the rhizome of the selected plant. Subsequent propagation has been performed by tissue culture. First propagation took place at a research greenhouse in Camporosso Mare, Italy in 2010 and has shown that the unique features of this cultivar are stable and reproduced true to type in multiple successive generations.

SUMMARY OF THE INVENTION

The cultivar 'ABALCHERA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABALCHERA' These characteristics in combination distinguish 'ABALCHERA' as a new and distinct *Ranunculus* cultivar:

1. Unique creamy peach flower color.
2. Exceptionally large flower.
3. Exceptionally long flower stem.

PARENT COMPARISON

Plants of the new cultivar 'ABALCHERA' are similar to plants of the seed parent, in most horticultural characteristics, however, plants of the new cultivar 'ABALCHERA' differ in the following;

1. Flower color. Flowers of the new variety are a mixture of Yellow-Orange 18D, and Red 37D. Flower color of the seed parent is vivid orange, near RHS 28B.
2. The new variety produces a larger flower, with an average diameter range of 10 to 12 cm, the seed parent has an average diameter range of 8 to 10 cm.

Plants of the new cultivar 'ABALCHERA' are similar to plants of the pollen parent, in most horticultural characteristics, however, plants of the new cultivar 'ABALCHERA' differ in the following;

1. Flower color. Flowers of the new variety are a mixture of Yellow-Orange 18D, and Red 37D. Flower color of the pollen parent is light purple-pink, near RHS 62C.
2. The new variety produces a larger flower, with an average diameter range of 10 to 12 cm, the pollen parent has a flower with an average diameter range of 8 to 10 cm.

COMMERCIAL COMPARISON

Plants of the new cultivar 'ABALCHERA' are comparable to the unpatented commercial variety *Ranunculus*

'ABGNOWEE'. The two *Ranunculus* varieties are similar in most horticultural characteristics; however, the new variety 'ABALCHERA' differs in the following:

1. Flower color of the new variety has shades of peach not found in this comparator.
2. Flower size of the new variety is larger.

BRIEF DESCRIPTION OF THE PHOTOGRAPHS

The accompanying photograph in FIG. 1 illustrates in full color flowering plants of the new variety at approximately five months old, grown in a greenhouse.

FIG. 2 illustrates a close up of plant parts.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart $6^{th}$ edition, except where general terms of ordinary dictionary significance are used. The following observations and measurements describe 'ABALCHERA' plants grown in a greenhouse Camporosso Mare, Italy. The plant described has been cultivated under glass, planted in the months of September and described in the month of February. One must always refer to these conditions of season and culture, when considering the present description. By reason of different climate or culture conditions, differences may arise between certain characteristics of the plant and the corresponding characteristics of the description. It should be considered as normal and do not modify the essence of the present invention because it will possible to identify the plant by means of the totality of the characteristics given in the description. The rhizome has been planted on raised benches in a peat and pumice substrate mixture. The growing temperature ranged from 12° C. to 25° C. during the day and from 2° C. to 8° C. during the night. General light conditions are bright, normal sunlight. Measurements and numerical values represent averages of typical plant types.

Botanical classification: *Ranunculus asiaticus* 'ABALCHERA'.

Propagation:

*Time to rooting.*—15 days at approximately 10-12° C.

*Time to produce a rooted plantlet.*—20 days.

*Root description.*—Secondary roots grow from the rhizome and are fasciculate type.

Plant:

*Growth habit.*—Herbaceous perennial, robust plant, semi-erect vegetation.

*Height to top flower.*—55 to 60 cm.

*Plant spread.*—50 to 70 cm.

*Growth rate.*—Medium.

*Branching characteristics.*—Simple or branched. Main floral stems grow from a basal rosette, with 1 or 2 lateral branches, each one of which has a flower.

*Length of lateral branches.*—30 to 40 cm.

*Diameter of lateral branches.*—0.6 to 0.8 cm.

*Texture of lateral branches.*—Glossy, slightly tomentose.

*Internode length.*—Internodes are extremely close together, forming a basal rosette.

*Strength of lateral branches.*—Medium.

*Color of lateral branches.*—Yellow Green (RHS 144A).

*Angle of branches.*—20° to 25° C.

*Number of leaves per lateral branch.*—Usually 2.

Foliage:

*Leaf.*—The leaves, usually numerous, have a marked heterophyllia, in relation to the degree of their development and their position on the plant (base of the plant; floral stem).

*Leaf at the base of the plant.*—Arrangement: Trifoliate (young leaf, YL); Biternate (mature leaf, ML). Average Length: 25 to 45 cm. Average Width: 15 to 25 cm. Overall Shape of blade: Obovate (young leaf); Palmatipartite (mature leaf). Dissected leaves, describe lobes, quantity of dissection: Young leaves are generally not lobed; mature leaves are generally divided in 3 parts, each one of which is further divided in 3 or more lobes. Apex: Rounded (young leaf); Acute (mature leaf). Base: Rounded. Attachment: Base of the plant. Margin: Dentate. Texture of top surface: Slightly tomentose. Texture of bottom surface: Slightly tomentose. Appearance of top surface: Glossy. Appearance bottom surface: Glossy. Leaf internode length: The internodes are extremely close together, forming a basal rosette. Color: Young foliage upper side: Green (RHS N137A). Young foliage under side: Green (RHS 137C). Mature foliage upper side: Green (RHS N137A). Mature foliage under side: Green (RHS 137C). Venation: Type: Dichotomous; plunging in to the limb at the upper surface; raised on the limb at the lower surface. Venation color upper side: Yellow Green (RHS 144A). Venation color under side: Yellow Green (RHS 144A). Petiole: Petiole: Long, tubular, rigid. Length: 15 to 25 cm. Diameter: 0.4 to 0.8 cm. Pubescence: Slightly tomentose. Color: Yellow Green (RHS 144A).

*Leaf inserted at the nodes of the floral stems (sl).*—Arrangement: Biternate. Average Length: 12.0 to 22.0 cm. Average Width: 14.0 to 18.0 cm. Overall Shape of blade: Palmatipartite. Dissected leaves, describe lobes, quantity of dissection: Generally divided in 3 parts, each one of which is further divided in many deeply incised lobes. Apex: Acute. Base: Acute. Attachment: Petiolate. Margin: Serrate. Texture of top surface: Slightly tomentose. Texture of bottom surface: Slightly tomentose. Appearance of top surface: Matte. Appearance bottom surface: Glossy. Leaf internode length: 5 to 10 cm. Color: foliage upper side: Green (RHS N137A). foliage under side: Yellow Green (RHS 137C). Venation: Type: Dichotomous, plunging in to the limb at the upper surface and raised on the limb at the lower surface. Venation color upper side: Yellow Green (RHS 144A). Venation color under side: Yellow Green (RHS 144A). Petiole: Petiole: Long, slightly flat, rigid. Length: 4 to 8 cm. Diameter: 0.5 to 0.8 cm. Pubescence: Slightly tomentose. Color: Yellow Green (RHS 144A); Purple (RHS N79B) near the attachment.

Flower:

*Bloom period.*—Winter to Spring.

*Vase life (cut flower).*—10-15 days.

*Persistent or self-cleaning.*—Self-Cleaning.

*Bud.*—Closed bud (CB): Shape: Flattened globular with a sharp point. Length: 1.4 to 1.6 cm. Diameter: 1.2 to 1.8 cm. Color: Green (RHS 137B) at the center; Yellow Green (RHS 145B) where the sepals start to overlap; Purple (RHS N79B) along the venation and near the base. Slightly open bud (OB): Shape: Flattened globular. Length: 1.7 to 2.2 cm. Diameter: 2.3 to 3.0 cm. Color: fades from Yellow Green (RHS 145C) to Yellow Orange (RHS 18C) from the base to the apex.

*Flower size* (*of*).—Diameter: 10 to 12 cm. Height: 3 to 6 cm.

*Corolla* (*of*).—Round, regular, in the form of a flat section. Petals: Arrangement: Arrangement: Imbricated, disposed on the receptacle in very tight verticils. The size of the petals is quite variable, according to the position in the corolla, decreasing from the exterior toward the center. The average size of fully developed petal is as follows: Lobe Length: 4.0 to 6.5 cm. Lobe Width: 5.0 to 5.5 cm. Quantity: Double flower, petals are very numerous (>100). Texture: Silky, thin, resistant. Lobe Apex: Rounded. Lobe shape: Obovate. Margin: Entire or finely Crenate. Aspect: Concave with moderately reflexed apex when flower is fully opened. Color when opening (CF): Upper surface: Yellow Orange (RHS 18B) fading to Red (RHS 38B) from the base towards the apex. Lower surface: Yellow (RHS 18B) fading to Red (RHS 38B) from the base towards the apex. Color Fully opened (OF): Upper surface (PU): Yellow Orange (RHS 18D) and Red (RHS 37D) pretty evenly mixed together. Lower surface (PL): Yellow Orange (RHS 18D) and Red (RHS 37D) pretty evenly mixed together.

*Calyx to sepals* (*s*).—Quantity per flower: 5 to 10. Shape: Concave, incurved at the apex. Length: 2.5 to 3.0 cm. Width: 1.0 to 1.5 cm. Apex: Acute, claw-like. Base: Flat. Margin: Entire. Texture: Lower surface is tomentose; Upper surface is glabrous. Color Upper Surface: Yellow Green (RHS 138B); Light Yellow Green (RHS 145B) near the base. Color Lower Surface: Greyish Green (N137A) at the apex; Green (RHS 137B); Purple (RHS N79B) along the venations and near the base.

*Peduncle.*—None.

*Pedicel.*—Length: 30 to 35 cm. Diameter: 1.1 to 1.3 cm. Color: Yellowish Green (RHS 144A). Orientation: Upright, straight, rigid. Pubescence: Slightly tomentose.

*Fragrance.*—None.

Reproductive organs:

*Androecium.*—Stamens: Almost completely transformed as petals.

*Gynoecium.*—The pistils are numerous, short, locked together at the center of the corolla in a Purple (RHS N79B), dome-shaped apocarpous gynoecium.

Other characteristics:

*Seeds and fruits.*—Seeds and fruit production not observed.

*Disease/pest resistance.*—Neither resistance nor susceptibility to normal diseases and pests of *Ranunculus* has been observed.

*Temperature tolerance.*—Upper and lower temperature tolerance not observed, plants have been grown in a climate controlled greenhouse. *Ranunculus asiaticus* typically tolerates temperatures within USDA Zones 7 to 11.

What is claimed is:

1. A new and distinct cultivar of *Ranunculus* plant named 'ABALCHERA' as herein illustrated and described.

* * * * *